US010539514B2

(12) United States Patent
Mori et al.

(10) Patent No.: US 10,539,514 B2
(45) Date of Patent: Jan. 21, 2020

(54) SUBSTRATE INSPECTION METHOD, COMPUTER STORAGE MEDIUM AND SUBSTRATE INSPECTION APPARATUS

(71) Applicant: Tokyo Electron Limited, Tokyo (JP)

(72) Inventors: Takuya Mori, Tokyo (JP); Makoto Hayakawa, Koshi (JP)

(73) Assignee: Tokyo Electron Limited, Tokyo (JP)

( * ) Notice: Subject to any disclaimer, the term of this patent is extended or adjusted under 35 U.S.C. 154(b) by 122 days.

(21) Appl. No.: 15/577,354

(22) PCT Filed: May 13, 2016

(86) PCT No.: PCT/JP2016/064250
§ 371 (c)(1),
(2) Date: Nov. 28, 2017

(87) PCT Pub. No.: WO2016/199539
PCT Pub. Date: Dec. 15, 2016

(65) Prior Publication Data
US 2018/0156739 A1 Jun. 7, 2018

(30) Foreign Application Priority Data

Jun. 8, 2015 (JP) .................................. 2015-115941

(51) Int. Cl.
*G01N 21/00* (2006.01)
*G01N 21/956* (2006.01)
(Continued)

(52) U.S. Cl.
CPC ....... *G01N 21/956* (2013.01); *G01N 21/9501* (2013.01); *H01L 21/67173* (2013.01); *H01L 21/67253* (2013.01)

(58) Field of Classification Search
None
See application file for complete search history.

(56) References Cited

U.S. PATENT DOCUMENTS 5,085,517 A * 2/1992 Chadwick ............ G01N 21/956
356/394
6,476,390 B1 * 11/2002 Murakoshi ........... G01N 23/225
250/306
(Continued)

FOREIGN PATENT DOCUMENTS

| JP | 2000-200356 A | 7/2000 |
| JP | 2004-165395 A | 6/2004 |
| JP | 2012-104593 A | 5/2012 |

OTHER PUBLICATIONS

International Search Report of the International Searching Authority dated Jul. 12, 2016 in corresponding international application No. PCT/JP2016/064250 (and English translation).

*Primary Examiner* — Shawn Decenzo
(74) *Attorney, Agent, or Firm* — Posz Law Group, PLC

(57) ABSTRACT

A method of inspecting a substrate to be repeatedly treated along a predetermined transfer way in a plurality of kinds of different treatment apparatuses, includes: imaging a substrate that has been treated in one of the treatment apparatuses, to acquire a first substrate image; imaging a substrate that has been an object for imaging the first substrate image and further treated in another treatment apparatus different from the one treatment apparatus after treated in the one treatment apparatus, to acquire a second substrate image; then performing defect inspection, based on the first substrate image and the second substrate image; and identifying, depending on whether or not a defect detected from the second substrate image is not detected from the first substrate image, whether or not the defect is caused by a treatment after the first substrate image is acquired and a treatment before the second substrate image is acquired.

7 Claims, 12 Drawing Sheets

(51) Int. Cl.
*G01N 21/95* (2006.01)
*H01L 21/67* (2006.01)

(56) References Cited

U.S. PATENT DOCUMENTS

| | | | | |
|---|---|---|---|---|
| 6,865,288 | B1* | 3/2005 | Shishido | G06T 7/001 |
| | | | | 382/141 |
| 7,048,602 | B2* | 5/2006 | Phelan | H01L 51/56 |
| | | | | 356/237.1 |
| 9,466,463 | B1* | 10/2016 | Lam | H01J 37/28 |
| 2002/0130262 | A1* | 9/2002 | Nakasuji | G01N 23/225 |
| | | | | 250/311 |
| 2004/0151993 | A1* | 8/2004 | Hasegawa | G03F 1/64 |
| | | | | 430/5 |
| 2005/0037272 | A1* | 2/2005 | Tanaka | G03F 7/70991 |
| | | | | 430/30 |
| 2010/0149505 | A1* | 6/2010 | Sewell | G03B 27/54 |
| | | | | 355/67 |
| 2015/0146968 | A1* | 5/2015 | Tien | G06T 7/001 |
| | | | | 382/149 |

* cited by examiner

FIG.8

| LOT NUMBER | TRANSFER WAY | | | | | | | | | |
|---|---|---|---|---|---|---|---|---|---|---|
| R1 | 2 | 3 | 6 | 4 | 3 | 6 | 2 | 3 | . | . |
| R2 | 2 | 3 | 2 | 3 | 6 | 4 | 5 | 3 | . | . |
| R3 | 2 | 3 | 6 | 4 | 5 | 2 | 3 | 6 | . | . |
| R4 | 2 | 3 | 6 | 4 | 2 | 3 | 6 | 4 | . | . |
| . | . | . | . | . | . | . | . | . | . | . |
| . | . | . | . | . | . | . | . | . | . | . |
| Rn | . | . | . | . | . | . | . | . | . | . |

| WAFER NUMBER | SUBSTRATE IMAGE KIND | DEFECT GROUP | TRANSFER ROUTE |
|---|---|---|---|
| R1-4 | P2-1 | E1 | 6、4 |
| R1-15 | P1-3 | E2 | 5、6 |
| R2-6 | P1-2 | E2 | 5、6 |
| R4-3 | P2-4 | E1 | 4 |
| R4-12 | P2-2 | E3 | 6、2、5 |
| R5-9 | P1-2 | E3 | 2 |
| . | | | . |
| . | | | . |
| . | | | . |
| . | | | . |
| . | | | . |
| . | | | . |
| . | | | . |
| . | | | . |
| . | | | . |
| . | | | . |

| WAFER NUMBER | TRANSFER WAY | | | | | | | | | |
|---|---|---|---|---|---|---|---|---|---|---|
| R1-1 | 2A | 3A | 6C | 4A | 3B | 6C | 2A | 3B | | ... |
| R1-2 | 2B | 3C | 6A | 4B | 3C | 6A | 2B | 3C | | ... |
| R1-3 | 2C | 3A | 6B | 4C | 3A | 6B | 2C | 3A | | ... |
| R1-4 | 2A | 3C | 6C | 4A | 3B | 6C | 2A | 3B | | ... |
| . | . | . | . | . | . | . | . | . | . | . |
| R3-4 | 2A | 3B | 6C | 4A | 5B | 2B | 3A | 6A | | . |
| R3-5 | 2B | 3C | 6B | 4C | 5A | 2B | 3A | 6B | | . |
| | | | | | | | | | | |
| | | | | | | | | | | |
| | | | | | | | | | | |

| WAFER NUMBER | SUBSTRATE IMAGE KIND | DEFECT GROUP | TRANSFER ROUTE |
|---|---|---|---|
| R1-4 | P2-1 | E1 | 6C, 4A |
| R1-15 | P1-3 | E2 | 5B, 6C |
| R2-6 | P1-2 | E2 | 5B, 6B |
| R4-3 | P2-4 | E1 | 4A |
| R4-12 | P2-2 | E3 | 6C, 2C, 5C |
| R5-9 | P1-2 | E3 | 2C |
| . | | | . |
| . | | | . |
| . | | | . |
| . | | | . |
| . | | | . |
| . | | | . |
| . | | | . |
| . | | | . |
| . | | | . |
| . | | | . |

DT

SUBSTRATE INSPECTION METHOD, COMPUTER STORAGE MEDIUM AND SUBSTRATE INSPECTION APPARATUS

CROSS REFERENCE TO RELATED APPLICATION

Technical Field

This application is based upon and claims the benefit of priority of the prior Japanese Patent Application No. 2015-115941, filed in Japan on Jun. 8, 2015, the entire contents of which are incorporated herein by reference.

The present invention relates to a method of inspecting a substrate, a computer-readable storage medium storing a program executing the inspection method, and a substrate inspection apparatus.

Background Art

In a manufacturing process of a semiconductor device, for example, various processing and treatments such as ion implantation processing, film-forming treatment, photolithography processing, and etching treatment are performed on a semiconductor wafer (hereinafter, referred to as a "wafer") as a substrate. The photolithography processing of forming a predetermined resist pattern on the wafer is performed in a coating and developing treatment apparatus equipped with various treatment apparatuses such as a resist coating apparatus which forms a resist film on the wafer, and a developing treatment apparatus which develops the resist film exposed into a predetermined pattern, and a transfer apparatus which transfers the wafer.

In the coating and developing treatment apparatus, an inspection apparatus which performs so-called macro defect inspection on the wafer is provided (Patent Document 1). In the macro defect inspection, the wafer subjected to predetermined treatments in the coating and developing treatment system is imaged, for example, by an imaging apparatus such as a CCD line sensor under predetermined illumination, whereby the imaged image of the wafer is acquired. Then, the acquired imaged image is compared with a wafer image being a reference, whereby the presence or absence of a defect is determined.

PRIOR ART DOCUMENT

Patent Document

[Patent Document 1] Japanese Laid-open Patent Publication No. 2012-104593

DISCLOSURE OF THE INVENTION

Problems to Be Solved by the Invention

Incidentally, the manufacturing process of the semiconductor device undergoes many processes as described above, so that if a defect is found in the macro defect inspection performed in the coating and developing treatment system, it is not easy to identify by which process the defect is caused. Therefore, there is a problem of requiring much time for identifying the cause of the defect and repairing the defect.

The present invention has been made in consideration of the point, and its object is to reduce the time required to identify a cause of a defect in a substrate treatment.

Means for Solving the Problems

To achieve the above object, the present invention is a substrate inspection method of inspecting a substrate to be repeatedly treated along a predetermined transfer way in a plurality of kinds of different treatment apparatuses, the substrate inspection method including: a first imaging step of imaging a front surface of a substrate that has been treated in one of the treatment apparatuses, to acquire a first substrate image; a second imaging step of imaging a front surface of a substrate that has been an object for imaging the first substrate image and further treated in another treatment apparatus different from the one treatment apparatus after treated in the one treatment apparatus, to acquire a second substrate image; a defect determination step of performing defect inspection, based on the first substrate image and the second substrate image, to determine presence or absence of a defect of the substrate; and a defect cause identification step of identifying, when a defect detected from the second substrate image is not detected from the first substrate image, the defect as being caused by a treatment after the first substrate image is acquired and a treatment before the second substrate image is acquired, and identifying, when the defect detected from the second substrate image is detected also from the first substrate image, the defect as being caused by a treatment before the first substrate image is acquired.

According to the present invention, a first substrate image is acquired by imaging a front surface of a substrate after treated in the treatment apparatus, and a second substrate image is further acquired after subsequent treatment is performed on the same substrate. Then, defect inspection is performed based on the first substrate image and the second substrate image to determine at which point in time the defect has occurred, thus making it possible to narrow down the steps to be investigated for identifying the step being the cause of the defect. Therefore, it is possible to reduce the time required to identify the cause of the defect in the substrate treatment.

The present invention according to another aspect is a computer-readable storage medium storing a program running on a computer of a control unit which controls a substrate processing system to cause the substrate processing system to perform the substrate inspection method.

The present invention according to still another aspect is a substrate inspection apparatus of inspecting a substrate to be repeatedly treated along a predetermined transfer way in a plurality of kinds of different treatment apparatuses, the substrate inspection apparatuses including: a first imaging apparatus which images a front surface of a substrate that has been treated in one of the plurality of kinds of different treatment apparatuses, to acquire a first substrate image; a second imaging apparatus which images a front surface of a substrate that has been an object for imaging the first substrate image and further treated in another treatment apparatus different from the one treatment apparatus after treated in the one treatment apparatus, to acquire a second substrate image; a defect determination unit which performs defect inspection on the substrate, based on the first substrate image and the second substrate image, to determine presence or absence of a defect of the substrate; and a defect cause identification unit which identifies, when a defect detected from the second substrate image is not detected from the first substrate image, the defect as being caused by a treatment after the first substrate image is acquired, and identifies, when the defect detected from the second substrate image is detected from the first substrate image, the defect as being caused by a treatment before the first substrate image is acquired.

Effect of the Invention

According to the present invention, it is possible to reduce the time required to identify a cause of a defect in a substrate treatment.

BRIEF DESCRIPTION OF THE DRAWINGS

FIG. 8 An explanatory view exemplifying a transfer recipe.

FIG. 9 An explanatory view exemplifying a defect determination table.

FIG. 12 An explanatory view exemplifying a transfer recipe according to another embodiment.

FIG. 13 An explanatory view exemplifying a defect determination table according to another embodiment.

BEST MODE FOR CARRYING OUT THE INVENTION

Figure 1:
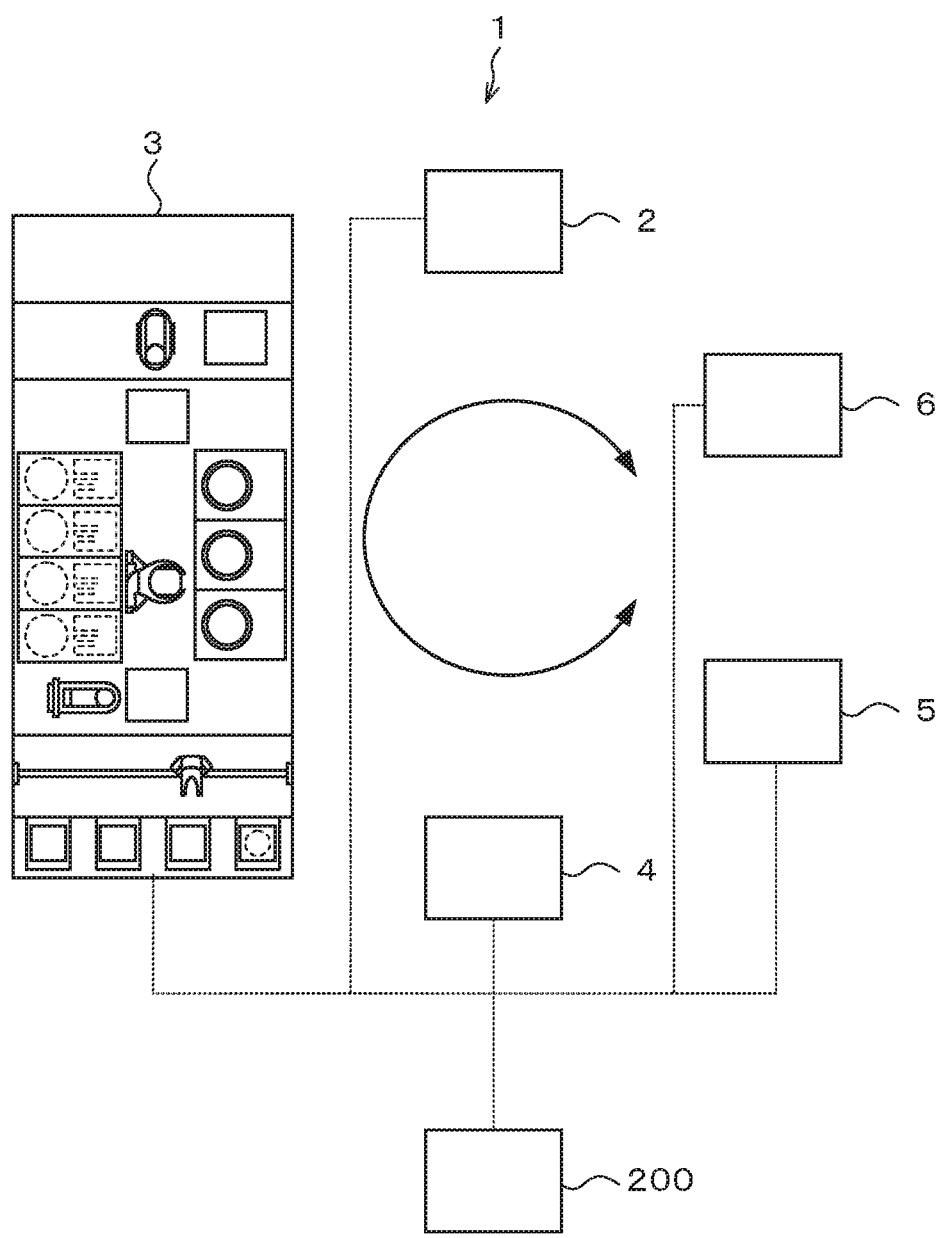
FIG. 1 An explanatory view illustrating the outline of a configuration of a substrate processing system according to an embodiment.

Hereinafter, an embodiment of the present invention will be described. FIG. 1 is an explanatory view illustrating the outline of a configuration of a substrate processing system 1 including a substrate inspection apparatus according to this embodiment. Note that in this specification and the drawings, components having substantially the same functional configurations are denoted by the same codes to omit duplicate description.

The substrate processing system 1 has, as illustrated in FIG. 1, for example, a film-forming treatment apparatus 2 which performs a film-forming treatment on the wafer, a coating and developing treatment apparatus 3 which performs a photolithography processing on the wafer, an etching treatment apparatus 4 which performs an etching treatment on the wafer, a planarization processing apparatus 5 which planarizes the wafer surface by performing a CMP (Chemical Mechanical Polishing) on the wafer, a rear surface cleaning apparatus 6 which cleans the rear surface of the wafer, and a later-described control apparatus 200 that controls the operations of the apparatuses.

As the film-forming treatment apparatus 2, for example, a plasma CVD apparatus that performs a film-forming treatment on the wafer by a plasma treatment, a so-called ALD (Atomic Layer Deposition) apparatus that performs a film-forming treatment by supplying a treatment gas into a treatment container or the like is used.

Figure 2:
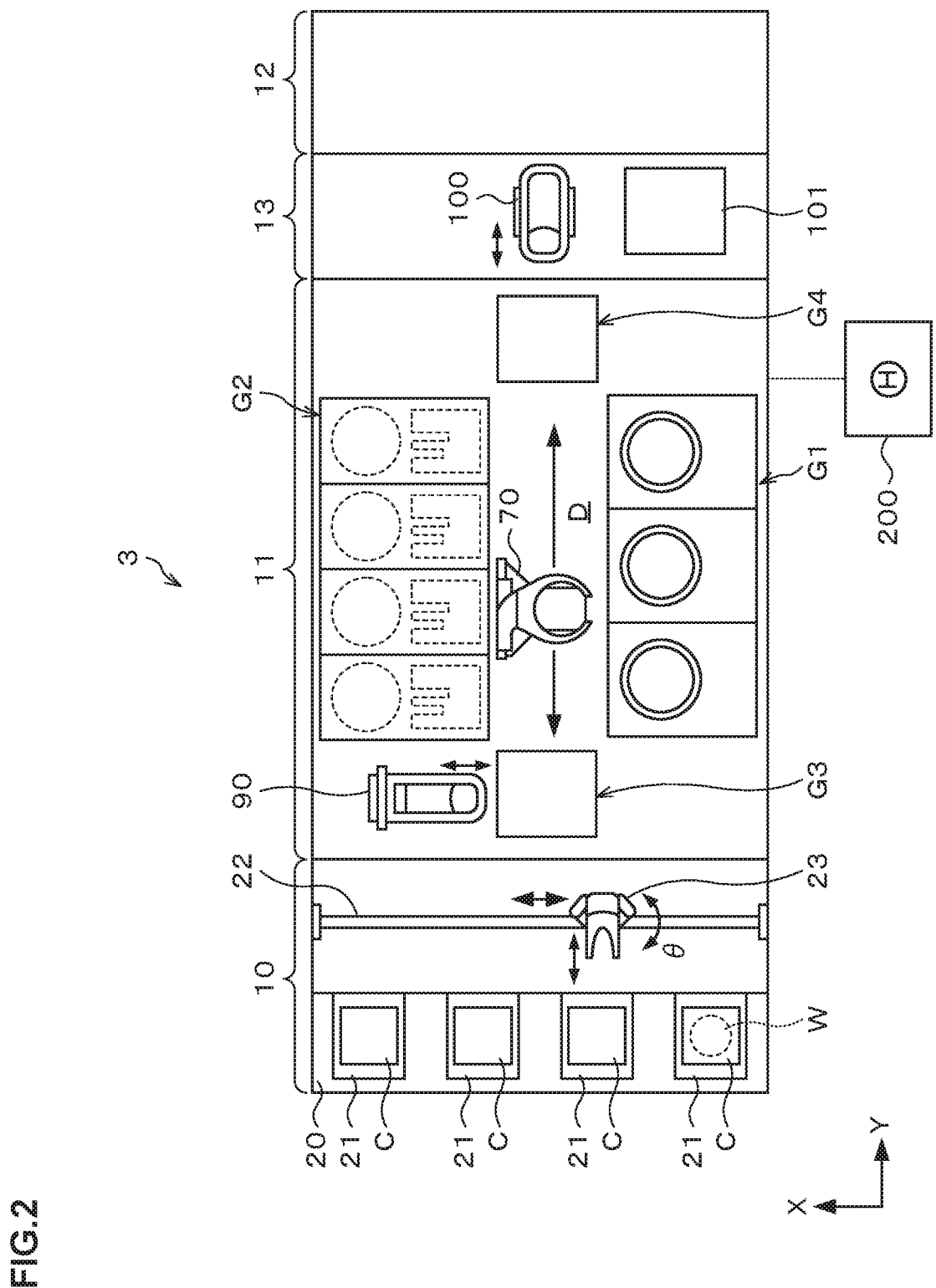
FIG. 2 A plan view illustrating the outline of the configuration of the substrate processing system according to this embodiment.

The coating and developing treatment apparatus 3 has, as illustrated in FIG. 2, a configuration in which a cassette station 10 into/out of which a cassette C housing a plurality of wafers W is transferred, a treatment station 11 which includes a plurality of various treatment apparatuses performing predetermined treatments on the wafer W, and an interface station 13 which delivers the wafer W to/from an exposure apparatus 12 adjacent to the treatment station 11, are integrally connected.

In the cassette station 10, a cassette mounting table 20 is provided. The cassette mounting table 20 is provided with a plurality of cassette mounting plates 21 on which the cassettes C are mounted when the cassettes C are transferred in/out from/to the outside of the coating and developing treatment apparatus 3. Note that the transfer of the wafer W among the film-forming treatment apparatus 2, the coating and developing treatment apparatus 3, the etching treatment apparatus 4, the planarization processing apparatus 5, and the rear surface cleaning apparatus 6 is performed by a transfer apparatus (not illustrated) which transfers the cassette C housing the wafers W.

In the cassette station 10, a wafer transfer apparatus 23 is provided which is movable on a transfer path 22 extending in an X-direction as illustrated in FIG. 2. The wafer transfer apparatus 23 is movable also in a vertical direction and around a vertical axis (in a θ-direction), and can transfer the wafer W between the cassette C on each of the cassette mounting plates 21 and a later-described delivery apparatus in a third block G3 in the treatment station 11.

In the treatment station 11, a plurality of, for example, four blocks G1, G2, G3, G4 are provided each including various apparatuses. For example, the first block G1 is provided on the front side (X-direction negative direction side in FIG. 2) in the treatment station 11, and the second block G2 is provided on the rear side (X-direction positive direction side in FIG. 2) in the treatment station 11. Further, the third block G3 is provided on the cassette station 10 side (Y-direction negative direction side in FIG. 2) in the treatment station 11, and the fourth block G4 is provided on the interface station 13 side (Y-direction positive direction side in FIG. 2) in the treatment station 11.

Figure 3:
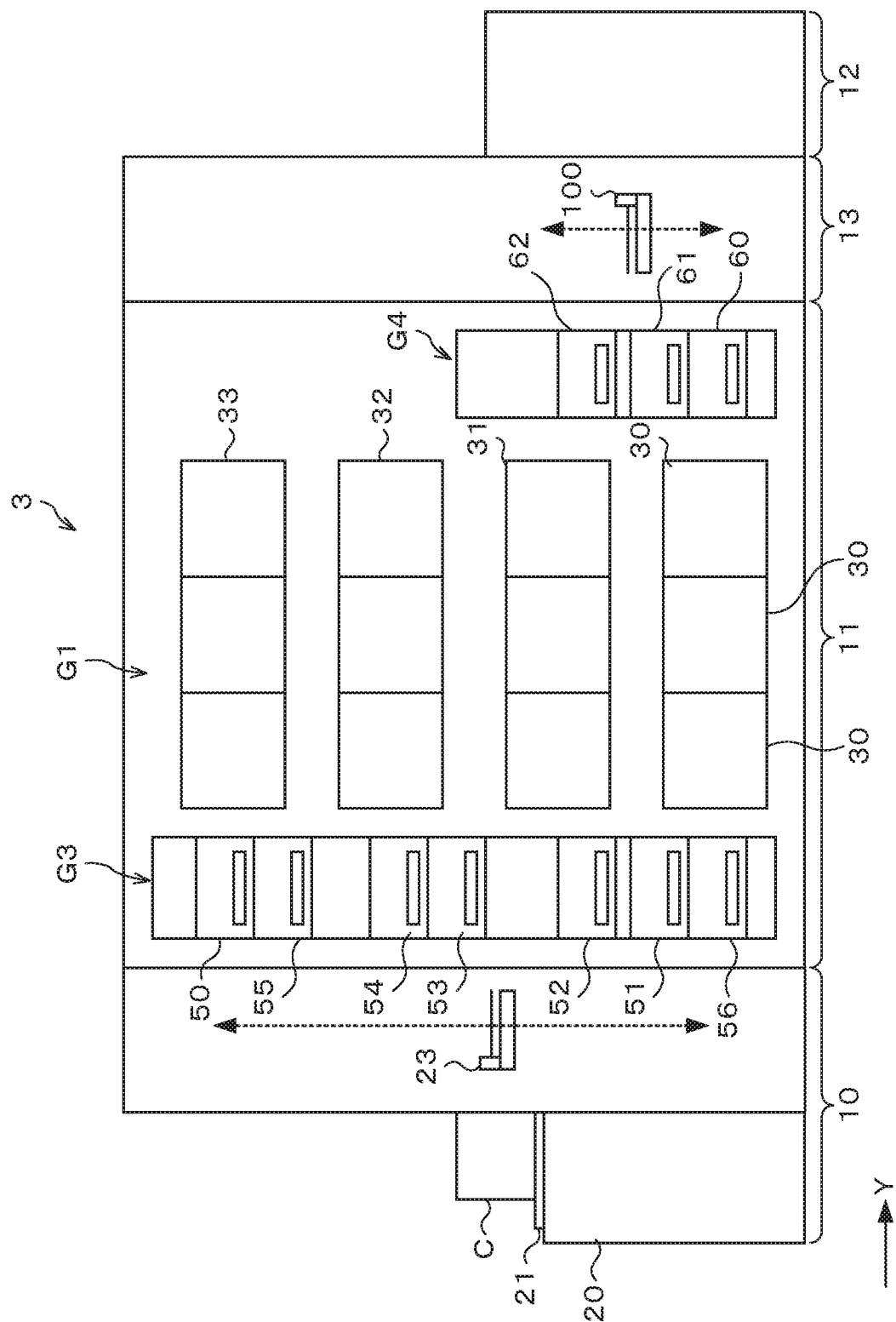
FIG. 3 A front view illustrating the outline of the configuration of the substrate processing system according to this embodiment.

For example, in the first block G1, as illustrated in FIG. 3, a plurality of solution treatment apparatuses, for example, developing treatment apparatuses 30 each of which performs a developing treatment on the wafer W, lower anti-reflection film forming apparatuses 31 each of which forms an anti-reflection film (hereinafter, referred to as a "lower anti-reflection film") at a lower layer of a resist film of the wafer W, resist coating apparatuses 32 each of which applies a resist solution to the wafer W to form a resist film, and upper anti-reflection film forming apparatuses 33 each of which forms an anti-reflection film (hereinafter, referred to as an "upper anti-reflection film") at an upper layer of the resist film of the wafer W, are arranged in order from the bottom.

For example, the developing treatment apparatuses 30, the lower anti-reflection film forming apparatuses 31, the resist coating apparatuses 32, and the upper anti-reflection film forming apparatuses 33 are arranged three each side by side in the horizontal direction. Note that the numbers and the arrangement of the developing treatment apparatuses 30, the lower anti-reflection film forming apparatuses 31, the resist coating apparatuses 32, and the upper anti-reflection film forming apparatuses 33 can be arbitrarily selected.

In each of the developing treatment apparatus 30, the lower anti-reflection film forming apparatus 31, the resist coating apparatus 32, and the upper anti-reflection film forming apparatus 33, for example, spin coating of applying a predetermined coating solution onto the wafer W is performed. In the spin coating, the coating solution is discharged, for example, from a coating nozzle onto the wafer W, and the wafer W is rotated to diffuse the coating solution over the front surface of the wafer W.

Figure 4:
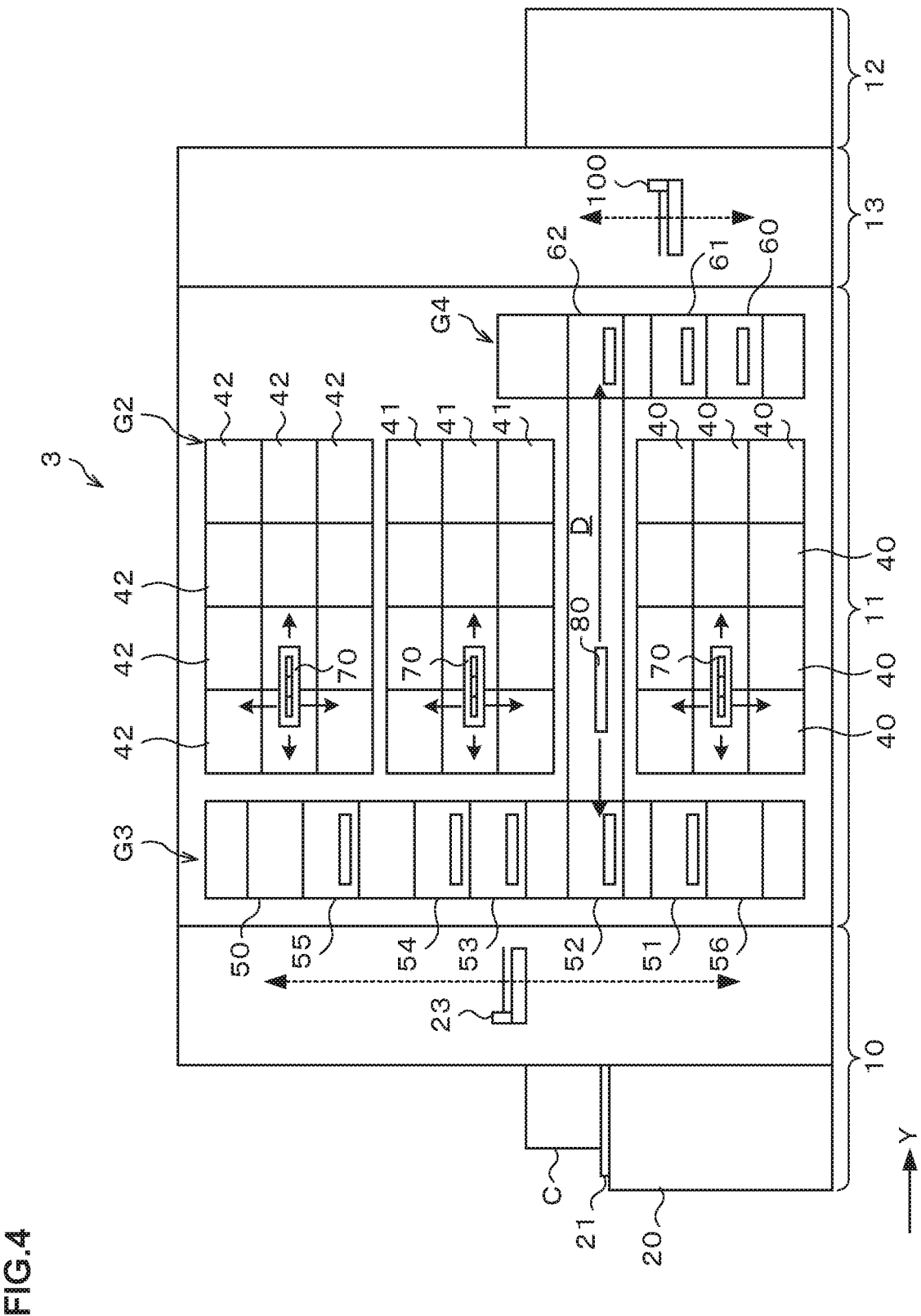
FIG. 4 A rear view illustrating the outline of the configuration of the substrate processing system according to this embodiment.

For example, in the second block G2, as illustrated in FIG. 4, thermal treatment apparatuses 40 each of which performs thermal treatments such as heating and cooling on the wafer W, adhesion apparatuses 41 each for enhancing adhesion between the resist solution and the wafer W, and edge exposure apparatuses 42 each of which exposes the outer peripheral portion of the wafer W, are provided side by side in the vertical direction and in the horizontal direction. The numbers and the arrangement of the thermal treatment apparatuses 40, the adhesion apparatuses 41, and the edge exposure apparatuses 42 can also be arbitrarily selected.

For example, in the third block G3, an inspection apparatus 50 which inspects the wafer W after being treated in the treatment station 11, a plurality of delivery apparatuses 51, 52, 53, 54, 55, and an inspection apparatus 56 which inspects the wafer W before being treated in the treatment station 11, are provided. Further, in the fourth block G4, a plurality of delivery apparatuses 60, 61, 62 are provided in order from the bottom. The configurations of the inspection apparatuses 50, 56 will be described later.

As illustrated in FIG. 2, a wafer transfer region D is formed in a region surrounded by the first block G1 to the fourth block G4. In the wafer transfer region D, for example, a plurality of wafer transfer apparatuses 70 are arranged each of which has a transfer arm movable, for example, in the Y-direction, the X-direction, the θ-direction, and the vertical direction. The wafer transfer apparatus 70 can move in the wafer transfer region D to transfer the wafer W to a predetermined apparatus in the first block G1, the second block G2, the third block G3 and the fourth block G4 therearound.

Further, in the wafer transfer region D, a shuttle transfer apparatus 80 is provided which linearly transfers the wafer W between the third block G3 and the fourth block G4.

The shuttle transfer apparatus 80 is configured to be linearly movable, for example, in the Y-direction in FIG. 4. The shuttle transfer apparatus 80 can move in the Y-direction while supporting the wafer W, and transfer the wafer W between the delivery apparatus 52 in the third block G3 and the delivery apparatus 62 in the fourth block G4.

As illustrated in FIG. 2, a wafer transfer apparatus 90 is provided adjacent on the X-direction positive direction side of the third block G3. The wafer transfer apparatus 90 has a transfer arm that is movable, for example, in the X-direction, the θ-direction, and the vertical direction. The wafer transfer apparatus 90 can move up and down while supporting the wafer W to transfer the wafer W to each of the delivery apparatuses in the third block G3.

In the interface station 13, a wafer transfer apparatus 100 and a delivery apparatus 101 are provided. The wafer transfer apparatus 100 has a transfer arm that is movable, for example, in the Y-direction, the θ-direction, and the vertical direction. The wafer transfer apparatus 100 can transfer the wafer W to/from each of the delivery apparatuses in the fourth block G4, the delivery apparatus 101 and the exposure apparatus 12, for example, while supporting the wafer W by the transfer arm.

Figure 5:
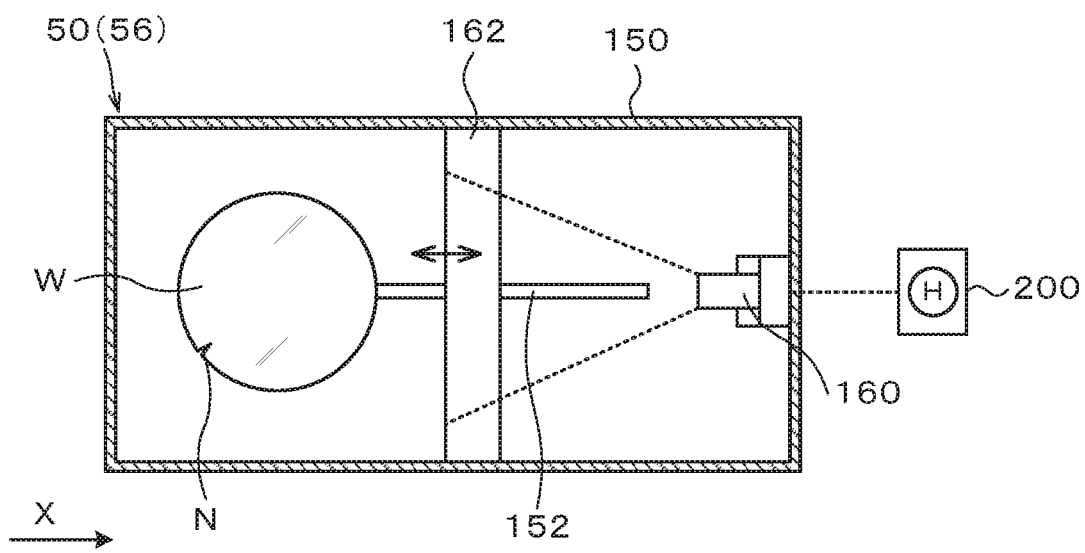
FIG. 5 A transverse sectional view illustrating the outline of a configuration of an inspection apparatus.
Figure 6:
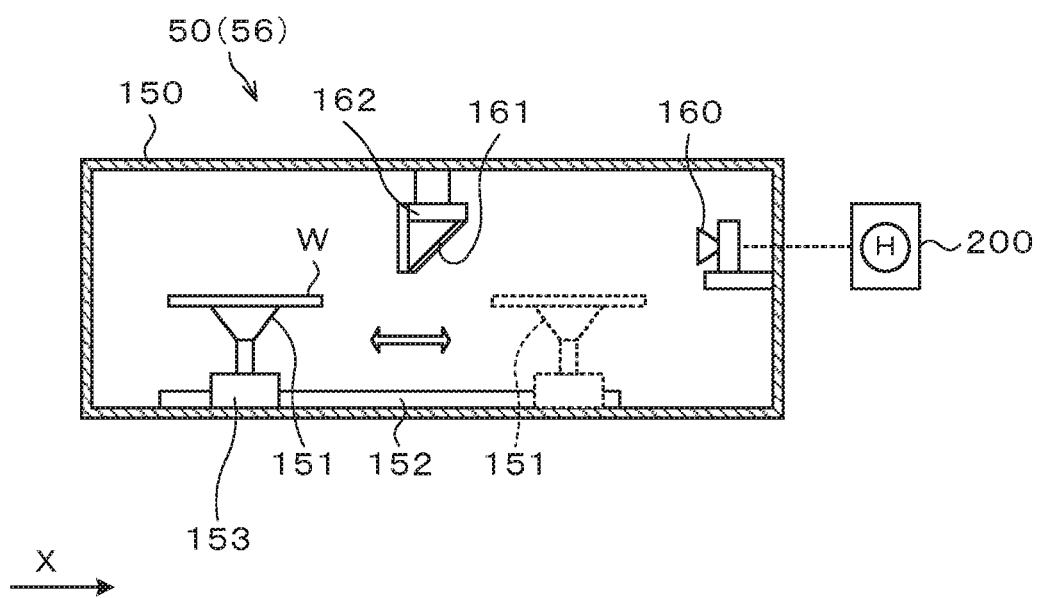
FIG. 6 A longitudinal sectional view illustrating the outline of the configuration of the inspection apparatus.

Next, a configuration of the above-described inspection apparatus 50 will be described. The inspection apparatus 50 has a casing 150 as illustrated in FIG. 5. Inside the casing 150, a wafer chuck 151 which holds the wafer W is provided as illustrated in FIG. 6. At the bottom surface of the casing 150, a guide rail 152 is provided which extends from one end side (an X-direction negative direction side in FIG. 5) to the other end side (an X-direction positive direction side in FIG. 5) in the casing 150. On the guide rail 152, a drive unit 153 is provided which rotates the wafer chuck 151 and is movable along the guide rail 152.

On a side surface on the other end side (the X-direction positive direction side in FIG. 5) inside the casing 150, an imaging unit 160 as a first imaging apparatus is provided. As the imaging unit 160, for example, a wide-angle CCD camera is used. Near the upper middle of the casing 150, a half mirror 161 is provided. The half mirror 161 is provided at a position facing the imaging unit 160 and in a such state that its mirror surface is inclined upward at 45 degrees toward the imaging unit 160 from a state of being directed vertically downward. Above the half mirror 161, an illumination device 162 is provided. The half mirror 161 and the illumination device 162 are fixed to the upper surface of the inside of the casing 150. The illumination from the illumination device 162 passes through the half mirror 161 and is applied downward. Accordingly, light reflected by an object existing below the illumination device 162 is further reflected by the half mirror 161 and captured into the imaging unit 160. In other words, the imaging unit 160 can image the object existing within an irradiation region by the illumination device 162. Then, the image of the wafer W (first substrate image) imaged by the imaging unit 160 of the inspection apparatus 50 is inputted into a later-described control apparatus 200.

Since the inspection apparatus 56 has the same configuration as that of the inspection apparatus 50, description of the inspection apparatus 56 will be omitted. Note that the imaging unit 160 of the inspection apparatus 56 functions as a second imaging apparatus of the present invention, and the image of the wafer W (second substrate image) imaged by the imaging unit 160 of the inspection apparatus 56 is similarly inputted into the control apparatus 200.

As the etching treatment apparatus 4, for example, an RIE (Reactive Ion Etching) apparatus which performs an etching treatment on the wafer W, for example, by a plasma treatment, a wet etching treatment apparatus which supplies a predetermined chemical to the wafer W, or the like is used.

Besides, in the rear surface cleaning apparatus 6, the rear surface of the wafer W is cleaned by bringing a brush for cleaning into contact with the rear surface of the wafer W and moving the brush relative to the wafer W while holding the wafer W.

In the above substrate processing system 1, the control apparatus 200 is provided as illustrated in FIG. 1. The control apparatus 200 is composed of a computer including, for example, a CPU, a memory and so on, and has a program storage unit (not illustrated). In the program storage unit, a program for controlling the inspection on the wafer W performed based on the substrate images imaged in the inspection apparatuses 50, 56 is stored. In addition, programs for realizing predetermined actions in the substrate processing system 1, namely, various processing and treatments such as the photolithography processing, etching treatment, CMP, rear surface cleaning treatment on the wafer W, by controlling the operations of the above-described various treatment apparatuses and the drive system such as the transfer apparatuses, are also stored in the program storage unit. Note that the programs may be the ones that are recorded, for example, in a computer-readable storage medium H such as a computer-readable hard disk (HD), flexible disk (FD), compact disk (CD), magneto-optical disk (MO), or memory card, and installed from the storage medium H into the control apparatus 200.

Figure 7:
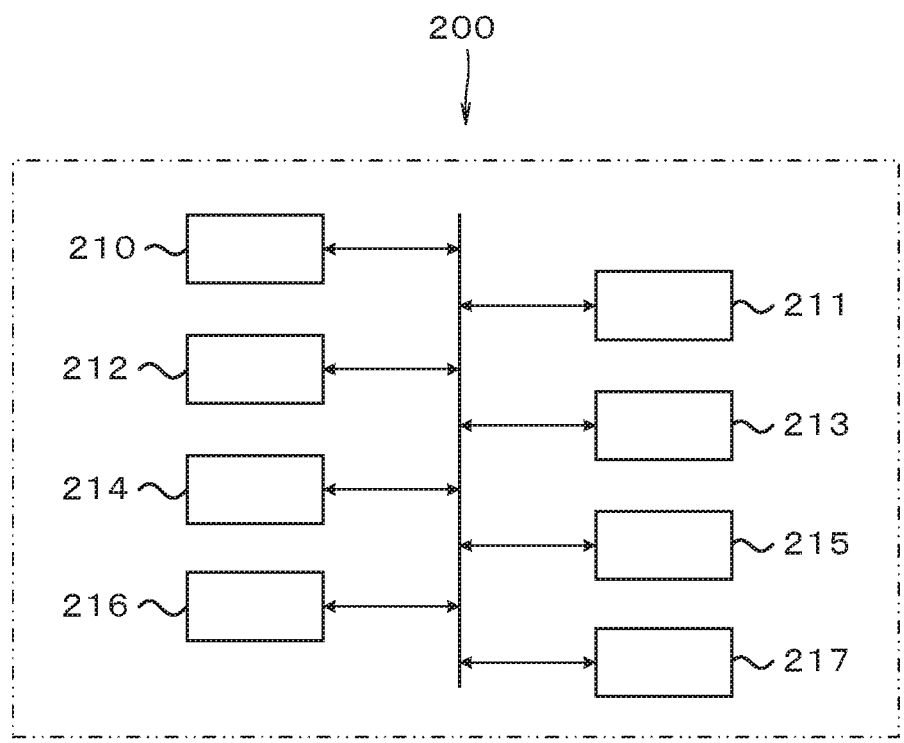
FIG. 7 A block diagram schematically illustrating the outline of a configuration of a control apparatus.

The control apparatus 200 also has, as illustrated in FIG. 7, a defect determination unit 210 which determines the presence or absence of a defect in the first substrate image and the second substrate image imaged by the imaging units 160 of the inspection apparatuses 50, 56, a defect information storage unit 211 which stores information on the defect detected by the defect determination unit 210, a defect classification unit 212 which classifies defects stored in the defect information storage unit 211 into a plurality of kinds, a transfer way storage unit 213 which stores transfer ways for the wafer W when the wafer W is repeatedly treated in the treatment apparatuses of the substrate processing system 1, a defect determination table generation unit 214 which generates a defect determination table in which the transfer ways for the wafer stored in the transfer way storage unit 213 and the kinds of the defects classified by the defect classification unit 212 are associated, and a defect cause identification unit 215 which identifies the treatment apparatus being a cause of defect generation.

In the defect determination unit 210, an inspection recipe is stored in advance, and the defect determination unit 210 determines the presence or absence of a defect in the first substrate image and the second substrate image, based on the inspection recipe. The inspection recipe is composed of, for example, imaging conditions when imaging is performed by the imaging unit 160 and a reference image being a reference of defect inspection. The reference image is generated by combining a plurality of substrate images and having no defect of the wafers W in a state of having been subjected to predetermined treatments. Further, the reference image is generated at each stage where the same wafer W is repeatedly treated in the treatment apparatuses according to a later-described transfer recipe and its substrate image is acquired by the imaging unit 160. In the defect determination unit 210, a plurality of inspection recipes corresponding to each reference image are stored. A corresponding inspection recipe is selected based on the later-described transfer recipe, and inspection is performed based on the selected inspection recipe.

In the defect information storage unit 211, information on the defect detected by the determination of the defect performed by the defect determination unit 210 at each stage of treatment on the same wafer W is stored.

In the defect classification unit 212, defects are classified into a plurality of kinds, based on the characteristic amounts of the defect information stored in the defect information storage unit 211. Here, the characteristic amounts of the defect information are, for example, information such as the size, shape, position of the defect detected by the defect determination unit 210, and the pixel value (luminance) of the substrate image, and defects having similar characteristic amounts are classified into groups.

In the transfer way storage unit 213, the transfer way for the wafer W to be treated in the substrate processing system 1 is stored, for example, as a transfer recipe TR illustrated in FIG. 8 in units of each lot Rn (n is an integer of 1 or more). The number of the lot Rn which has been subjected to the treatments is listed in the vertical row of the transfer recipe TR in FIG. 8, and the numbers of the treatment apparatuses which have performed the treatments on the wafer W, namely, the respective numbers of the film-forming treatment apparatus 2, the coating and developing treatment apparatus 3, the etching treatment apparatus 4, the planarization processing apparatus 5, and the rear surface cleaning apparatus 6 are listed from the left side to the right side in the horizontal column for each lot Rn in the order of the treatments. Note that the transfer way for the wafer W is not limited to the contents of this embodiment, but can be arbitrarily set according to the kinds or the like of the treatment apparatuses installed in the substrate processing system 1.

The above-described inspection recipe stored in the defect determination unit 210 and the reference image that is the base of the inspection recipe will be further described here. As described above, the reference image is generated at each stage where the same wafer W is repeatedly treated in the treatment apparatuses according to the transfer recipe TR and the substrate image thereof is acquired by the imaging unit 160. The "stage where the substrate image is acquired" means that the time when the wafer W passes through the coating and developing treatment apparatus 3 including the inspection apparatuses 50, 56 equipped with the imaging units 160. Therefore, explaining, for example, the wafer W relating to a lot R1 as an example, the wafer W is first transferred from the film-forming treatment apparatus 2 to the coating and developing treatment apparatus 3, and the first substrate image is acquired first in the inspection apparatus 50 after the treatment in the coating and developing treatment apparatus 3. Therefore, one inspection recipe is prepared based on the reference image generated in advance corresponding to the first substrate image at this stage. Further, the wafer W transferred out of the coating and developing treatment apparatus 3 is transferred again to the coating and developing treatment apparatus 3 via the rear surface cleaning apparatus 6 and the etching treatment apparatus 4. Accordingly, the wafer W transferred into the coating and developing treatment apparatus 3 is subjected to acquisition of its second substrate image in the inspection apparatus 56. Then, based on a reference image generated in advance corresponding to the second substrate image at this stage, an inspection recipe different from the above-mentioned one inspection recipe is prepared. Similarly, after the acquisition of the second substrate image, the wafer W treated in the coating and developing treatment apparatus 3 is imaged in the inspection apparatus 50 so that the first substrate image of the same wafer W is acquired for the second time. Thereafter, the wafer W transferred again into the coating and developing treatment apparatus 3 through the rear surface cleaning apparatus 6 and the film-forming treatment apparatus 2 is imaged in the inspection apparatus 56 so that the second substrate image of the wafer W is acquired for the second time. Inspection recipes are prepared in advance corresponding to the first substrate image for the second time and the second substrate image for the second time. Note that the reason why the inspection recipe is prepared for each stage where the substrate image is acquired by the imaging unit 160 is to improve the accuracy of the defect inspection, and the inspection recipe does not always need to be provided for each stage of acquiring the imaged image as in this embodiment.

In the defect determination table generation unit 214, for example, a defect determination table DT illustrated in FIG. 9 is generated in which the transfer recipes TR stored in the transfer way storage unit 213 and the kinds of the defects classified by the defect classification unit 212 are associated.

The "wafer number" listed in defect determination table DT illustrated in FIG. 9 means, for example, in what number wafer W in a lot Rn the defect has been detected. For example, "R1-4" means the fourth wafer in the lot R1. The "substrate image kind" means on what number the first substrate image P1 or the second substrate image P2 has been acquired. For example, "P2-1" means the second substrate image P2 acquired first of the second substrate images P2. The "defect group" means a group En into which defects having similar characteristic amounts are classified by the defect classification unit 212. FIG. 9 shows a case in which, for example, three kinds of defect groups E1, E2, E3 have been detected. Besides, the "transfer route" lists the number of the treatment apparatus through which the wafer W has passed directly before its substrate image having a detected defect is acquired, more specifically, the treatment apparatus through which the wafer W has passed between a substrate image imaged directly before the substrate image having a detected defect and the substrate image having a detected defect. For example, taking a second substrate image "P2-4" listed in FIG. 9 as an example, the substrate image directly before the second substrate image "P2-4" is a first substrate image "P1-4", and means that the treatment apparatus through which the wafer W has passed after the first substrate image P1-4 was acquired until the time when the second substrate image P2-4 is acquired is the etching treatment apparatus 4 of "4". Note that because the wafer W necessarily passes through the coating and developing treatment apparatus 3 for acquisition of the substrate image, the description of the number "3" is omitted in FIG. 9.

The defect cause identification unit 215 identifies the treatment apparatus that is a cause of defect generation when a defect is detected by the defect determination unit 210. When the substrate whose defect has been detected corresponds to a second substrate image P2-n, the defect cause identification unit 215 determines first whether or not a defect has been detected in a first substrate image P1-(n−1) acquired directly before the second substrate image P2-n. Then, when the defect detected from the second substrate image P2-n is not detected from the first substrate image P1-(n−1), this defect is identified as being caused by a treatment after the first substrate image P1-(n−1) is acquired and before the second substrate image P2-n is acquired. Besides, when the defect detected from the second substrate image P2-n is detected from the first substrate image P1-(n−1), this defect is identified as being caused by a treatment before the first substrate image P1-(n−1) is acquired. Thus, it is possible to identify at what point in time, namely, through what treatment apparatus the wafer W has passed and thereby has the defect caused.

Then, the defect cause identification unit 215 identifies the treatment apparatus which has become the cause of the defect, on the basis of the defect determination table DT. For example, the substrate image "P2-1" of the wafer number "R1-4" and the substrate image "P2-4" of the wafer number "R4-3" in FIG. 9 are classified into the same defect group E1, and the wafers W have passed in common through the etching treatment apparatus 4. Therefore, the defect relating to the defect group E1 can be estimated to be caused by the etching treatment apparatus 4. Then, when it is confirmed that the etching treatment apparatus 4 is roughly probably a cause of the result, by accumulating the defect information and inspecting the etching treatment apparatus 4 at occurrence of the defect group E1, the etching treatment apparatus 4 is identified as being the treatment apparatus which has become the cause of the defect.

Next, the treatments on the wafer W and the inspection method of the wafer W performed using the substrate processing system 1 configured as described above will be described.

First, a cassette C housing a plurality of wafers W in the same lot Rn is transferred into the substrate processing system 1, and the wafers W are successively subjected, for example, to the film-forming treatment in the film-forming treatment apparatus 2. Then, the wafers W for which the film-forming treatment has been completed are each transferred into the cassette station 10 of the coating and developing treatment apparatus 3, and then transferred to the treatment station 11 in which the wafer W is temperature-regulated in the thermal treatment apparatus 40, then subjected to formation of a lower anti-reflection film in the lower anti-reflection film forming apparatus 31, and then transferred into the adhesion apparatus 41 in which the wafer W is subjected to the adhesion treatment. Note that when the wafer W is transferred to the treatment station 11, the second substrate image may be imaged in the inspection apparatus 56.

Then, the wafer W is subjected to formation of a resist film in the resist coating apparatus 32 and then subjected to formation of an upper anti-reflection film in the upper anti-reflection film forming apparatus 33. Then, the wafer W is subjected to edge exposure processing in the edge exposure apparatus 42, and subjected to exposure processing in the exposure apparatus 12. The wafer W is then transferred to the developing treatment apparatus 30 and subjected to a developing treatment, with which a series of photolithography processing in the treatment station 11 ends. The wafer W for which the photolithography processing has been completed is transferred to the inspection apparatus 50, and its first substrate image P1-1 is acquired by the imaging unit 160 (first imaging step). The wafers W for which the imaging in the inspection apparatus 50 has been completed are successively housed in the cassette C.

In addition, the defect determination unit 210 of the control apparatus 200 determines the presence or absence of a defect on the basis of the first substrate image P1-1. Then, for example, in the case where it is determined that there is a defect at this point in time and the level of the defect is not allowable, the treatments thereafter are stopped for the wafer W housed in the cassette C. When the defect is at an allowable level, the treatments are continuously carried on for the wafer W.

Then, the wafer W for which the treatments in the coating and developing treatment apparatus 3 have been completed is transferred to a treatment apparatus which performs a next treatment according to the transfer recipe TR, and subjected to a predetermined treatment. The wafer W subjected to the predetermined treatment is then transferred again into the coating and developing treatment apparatus 3 and subjected to a series of photolithography processing. The wafer W transferred to the coating and developing treatment apparatus 3 is subjected to acquisition of a second substrate image P2-1 in the inspection apparatus 56 when the wafer W is transferred to the treatment station 11 (second imaging step).

Then, the defect determination unit 210 determines the presence or absence of a defect, based on the second substrate image P2-1. Then, for example, in the case where it is determined that there is a defect at this point in time and the level of the defect is not allowable, the treatments thereafter are stopped for the wafer W and housed in the cassette C. In the case where the defect is at an allowable level, the treatments are continuously carried on for the wafer W. In addition, the defect cause identification unit 215 determines whether or not this defect is the one detected in the first substrate image P1-1. Then, when defects detected from the second substrate image P2-1 are, for example, only the ones detected in the first substrate image P1-1, no particular defect is identified as occurring in the treatments between acquisition of the first substrate image P1-1 and acquisition of the second substrate image P2-1. Contrarily, when defects detected from the second substrate image P2-1 include the one not detected in the first substrate image P1-1, the defect is identified as having occurred caused by the treatments between acquisition of the first substrate image P1-1 and acquisition of the second substrate image P2-1 (defect cause identification step). Further, in this event, the defect cause identification unit 215 identifies the treatment apparatus being a cause of the defect generation on the basis of the defect determination table DT. Note that when the information accumulated in the defect determination table DT is not sufficient, the accumulation of information in the defect determination table DT may be continued and the identification of the cause based on the defect determination table DT may be successively performed in the defect inspection of the subsequent wafers W.

Then, the wafers W are each subjected to repeated treatments in the various treatment apparatuses according to the transfer recipe TR, and its substrate image is acquired every time when the wafer W passes through the coating and developing treatment apparatus 3 and subjected to repeated defect inspection, with which a series of wafer treatment ends.

According to the above embodiment, the first substrate image P1 is acquired by imaging the front surface of the wafer W after being treated in the various treatment apparatuses in the substrate processing system 1, and the second substrate image P2 is further acquired after the subsequent treatments are performed on the same wafer W. Then, defect inspection is performed based on the first substrate image P1 and the second substrate image P2 to determine at which point in time the defect has occurred, thus making it possible to narrow down the steps to be investigated for identifying the step being the cause of the defect. Therefore, it is possible to reduce the time required to identify the cause of the defect in the treatments in the substrate processing system 1.

Further, generation of the defect determination table DT performed by the defect determination table generation unit 214 on the basis of the result of the defect inspection and identification of the treatment apparatus being the cause of the defect generation on the basis of the defect determination table DT makes it possible to quickly identify the treatment being the cause of the defect and the treatment apparatus relating to the treatment.

Note that, for example, the wafer W determined to have a defect, as a result of inspection in the inspection apparatuses 50, 56 on the wafer W after being treated in the substrate processing system 1, is possibly subjected to correction of the defect by rework after transferred out of the substrate processing system 1 and transferred again into the substrate processing system 1. In this case, unless by which treatment the defect is caused can be identified, the defect is not solved even when the rework is performed or the rework is performed also on a portion having no defect. In this regard, identification of the cause of the defect by the defect cause identification unit 215 makes it possible to efficiently perform the rework treatment so as to improve the yield and productivity of the wafer treatment in the present invention.

Though the control apparatus 200 is provided in common to the treatment apparatuses in the substrate processing system 1 in the above embodiment, individual control apparatuses (not illustrated) may be provided, for example, for the film-forming treatment apparatus 2, the coating and developing treatment apparatus 3, the etching treatment apparatus 4, the planarization processing apparatus 5, and the rear surface cleaning apparatus 6 respectively, and the control apparatuses may locally control the treatment apparatuses and communicate only necessary information with the treatment apparatus 200.

Further, though the defect determination unit 210 performs inspection on each of the first substrate image P1 and the second substrate image P2 in the above embodiment, a difference image between the first substrate image P1 and the second substrate image P2 may be used from the viewpoint of investigating whether or not the defect has occurred in the treatments between acquisition of the first substrate image P1 and acquisition of the second substrate image P2. In this case, an image save unit 216 which saves the first substrate images P1 and the second substrate images P2, and a difference image generation unit 217 which generates a difference image between the first substrate image P1 and the second substrate image P2 saved in the image save unit 216 are provided as illustrated, for example, in FIG. 7. As the inspection recipe, the one based on the reference image generated by combining difference images is used.

Employment of the difference images as the reference image ensures that when the defect determination unit 210 determines that there is a defect, the defect is determined to be caused by the treatments between acquisition of the first substrate image P1 and acquisition of the second substrate image P2. More specifically, when a defect exists in the first substrate image P1 of the wafer W to be inspected, the defect exists also in the second substrate image. Generation of the difference image between the first substrate image and the second substrate image enables removal of the defect originally existing in the first substrate image P1 from the difference image. Accordingly, the defect on the difference image can be determined to be caused by the treatments between acquisition of the first substrate image P1 and acquisition of the second substrate image P2.

Though the inspection apparatus 50 which inspects the wafer W before being treated in the treatment station 11 and the inspection apparatus 56 which inspects the wafer W after being treated in the treatment station 11 are used for inspecting a defect of the wafer W in the above embodiment, the specifications of the devices in the inspection apparatus 50 and the inspection apparatus 56 are preferably the same. More specifically, when the specifications of the devices in the inspection apparatus 50 and the inspection apparatus 56 are the same, it is possible to avoid occurrence of a difference between the first substrate image P1 and the second substrate image P2 caused by the difference in specifications. As a result, more accurate defect inspection can be performed.

Figure 10:
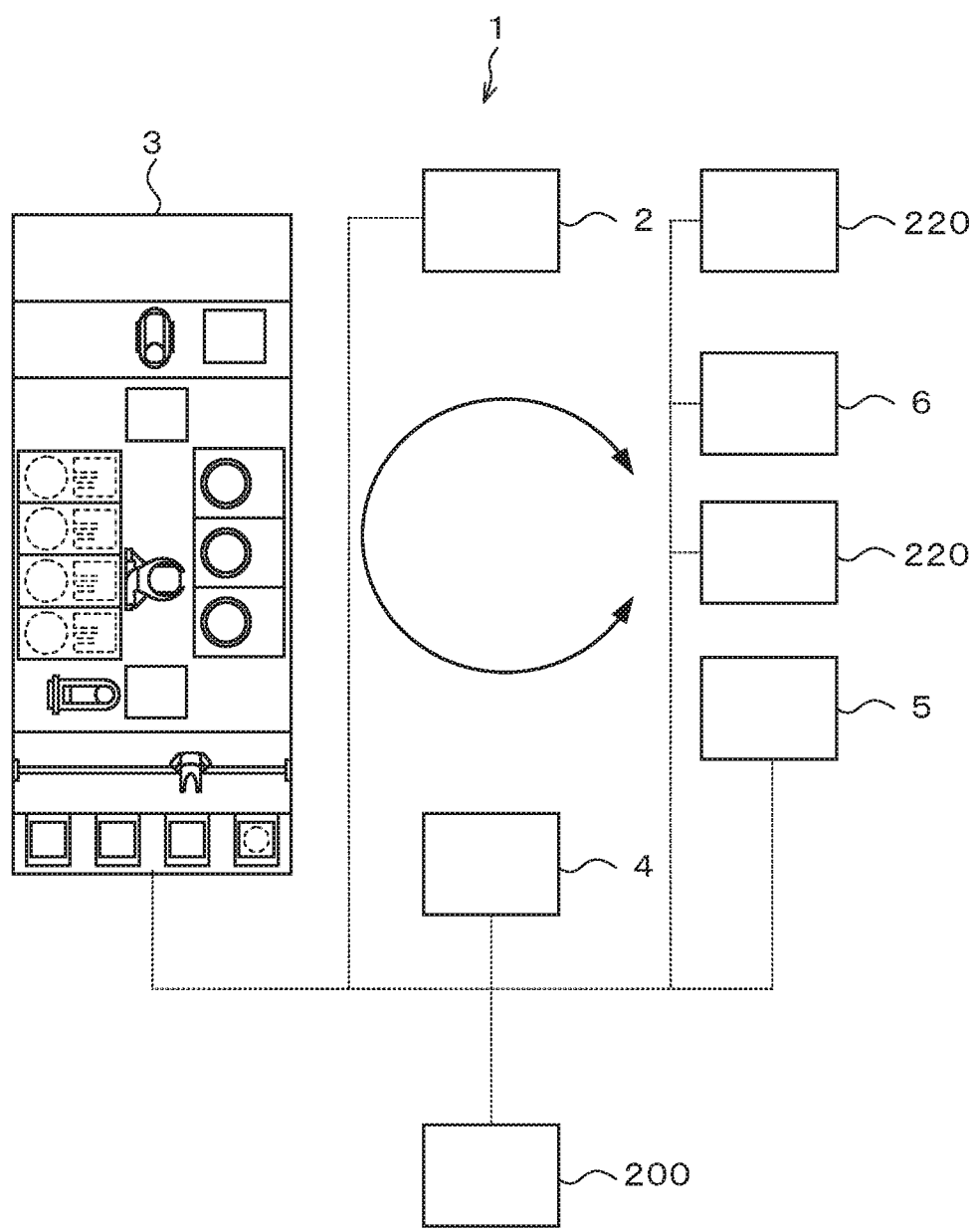
FIG. 10 An explanatory view illustrating the outline of a configuration of a substrate processing system according to another embodiment.

Though the imaging units 160 are provided only in the coating and developing treatment apparatus 3 in the above embodiment, the installation place and the number of installation of the imaging units 160 are not limited to the contents of this embodiment, but the imaging unit 160 can be arbitrarily set. More specifically, inspection apparatuses 220 having the same configuration as those of the inspection apparatuses 50, 56 may also be provided outside the coating and developing treatment apparatus 3, for example, as illustrated in FIG. 10 to acquire substrate images in the inspection apparatuses 220. For example, in the case where the imaging units 160 are provided only in the coating and developing treatment apparatus 3, the wafer W passes through a plurality of treatment apparatuses from when the wafer W is transferred out of the coating and developing treatment apparatus 3 until when the wafer W is transferred again into the coating and developing treatment apparatus 3 as listed in the defect determination table DT in FIG. 9, and therefore it is necessary to accumulate defect information until it becomes possible to determine that a specific treatment apparatus is the cause of the defect on the basis of the defect determination table DT. More specifically, for example, when the number of the treatment apparatuses listed in the "transfer route" is large as in the case of the wafer number R1-4 in the defect determination table DT in FIG. 9, the information on the defect necessary for identifying the defect by the defect determination table DT increases. On the other hand, increasing the number of installation of the imaging units 160, acquiring the substrate image every time when the treatment is performed in one treatment apparatus, and performing defect inspection based on the substrate image makes it possible to quickly determine that the treatment performed directly before the substrate image from which the defect has been detected is the cause of the defect.

Figure 11:
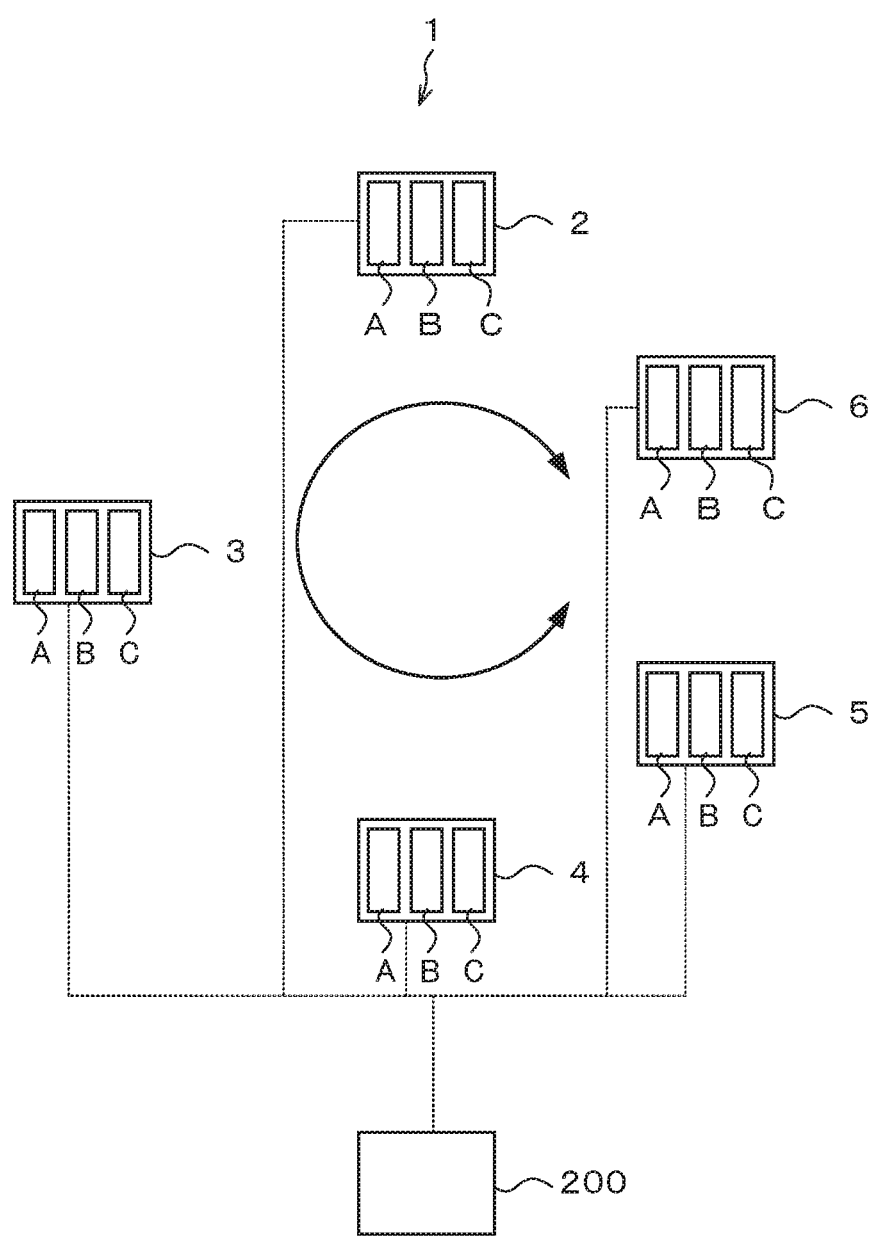
FIG. 11 An explanatory view illustrating the outline of a configuration of a substrate processing system in the case where a plurality of modules are provided in each treatment apparatus.

Though the film-forming treatment apparatus 2, the coating and developing treatment apparatus 3, the etching treatment apparatus 4, the planarization processing apparatus 5, and the rear surface cleaning apparatus 6 are provided one each in the substrate processing system 1 in the above-described embodiment, a plurality of each of the treatment apparatuses 2, 3, 4, 5, 6 are provided as illustrated in FIG. 11, for example, in the substrate processing system 1 actually installed in a clean room so that treatments are performed in parallel in some cases. Note that FIG. 11 illustrates a state in which the treatment apparatuses 2, 3, 4, 5, 6 are provided three each, and the three treatment apparatuses are discriminated separately as modules A, B, C. In this case, to solve the cause of the defect, it is necessary to identify which of the treatment apparatuses 2, 3, 4, 5, 6 the treatment apparatus being the cause of the defect is and then to further identify which of the three modules A, B, C the treatment apparatus being the cause of the defect is.

Hence, in the case where the plurality of modules A, B, C are provided in each of the treatment apparatuses, which of the modules A, B, C in each of the treatment apparatuses, to which each wafer W was transferred, has performed the treatment is stored in the transfer recipe TR as illustrated in FIG. 12. Note that FIG. 12 lists which module of which treatment apparatus has performed the treatment by combination of the number of the treatment apparatus and the number of the module such as the module A of the film-forming treatment apparatus 2 as "2A" and the module B of the film-forming treatment apparatus 2 as "2B".

Further, it is assumed that defects classified into the same defect group E1 are detected from the substrate image "P2-1" of the wafer number "R1-4" and from the substrate image "P2-4" of the wafer number "R4-3" as in the above case, and the wafers W have passed in common through the etching treatment apparatus 4. In this case, the defect cause identification unit 215 estimates the defects relating to the defect group E1 to be caused by the etching treatment apparatus 4 on the basis of the defect determination table DT. The defect cause identification unit 215 then further refers to the transfer recipe TR in FIG. 12. Then, the second substrate image P2-1 is the one acquired when the wafer W is transferred to a coating and developing treatment apparatus 3B for the second time indicated by hatching in FIG. 12 (the first substrate image P1-1 is acquired as described above in a coating and developing treatment apparatus 3C for the first time), showing that the etching treatment performed between the first substrate image P1-1 and the second substrate image P2-1 is performed by the module A of the etching treatment apparatus 4. Thus, the defect cause identification unit 215 can identify, from the information, the module A of the etching treatment apparatus 4 as the module being the cause of the defect.

Note that the method of identifying the module being the cause of the defect is not limited to the above method, but the those skilled in the art can reach various methods of identifying the module on the basis of the information on the transfer recipe TR and the defect determination table DT. One conceivable example is to generate the defect determination table DT as illustrated in FIG. 13 in which the information on the modules are added to the defect determination table DT illustrated in FIG. 9 by acquiring also the information on the modules A, B, C from the transfer recipe TR, at the time when the defect determination table generation unit 214 generates the defect determination table DT. From the substrate images relating to the wafer number "R1-15" and the wafer number "R2-6" listed in FIG. 13, defects classified in common into a defect group E2 are detected, and both wafers have passed through the planarization processing apparatus 5 and the rear surface cleaning apparatus 6, but the wafer W of the number "R1-15" has passed through the module C and the wafer W of the number "R2-6" has passed through the module B of the rear surface cleaning apparatus 6, showing that the wafers have been treated in the different modules. On the other hand, both the wafers have passed through the module B of the planarization processing apparatus 5. Consequently, the defect cause identification unit 215 can identify the module B of the planarization processing apparatus 5 through which both the wafers W have passed in common as the module being the cause of the defects on the basis of the defect determination table DT illustrated in FIG. 13.

Though the first substrate image and the second substrate image are acquired in the different inspection apparatuses 50, 56 respectively in the above embodiment, the first substrate image and the second substrate image do not always need to be acquired in the different inspection apparatuses but may be acquired in the same inspection apparatus. However, the wafer W before being treated in the treatment station 11 and the wafer W after being treated are preferably imaged in separate and independent inspection apparatuses from the viewpoint of interference between transfer routes and throughput of the wafer W.

Preferred embodiments of the present invention have been described above with reference to the accompanying drawings, but the present invention is not limited to the embodiments. It should be understood that various changes and modifications are readily apparent to those skilled in the art within the scope of the spirit as set forth in claims, and those should also be covered by the technical scope of the present invention. The present invention is not limited to the embodiments but can take various forms. The present invention is also applicable to the case where the substrate is a substrate other than the wafer, such as an FPD (Flat Panel Display), a mask reticle for a photomask or the like.

EXPLANATION OF CODES 1 substrate processing system
2 film-forming treatment apparatus
3 coating and developing treatment apparatus
4 etching treatment apparatus 5 planarization processing apparatus
6 rear surface cleaning apparatus
30 developing treatment apparatus
31 lower anti-reflection film forming apparatus
32 resist coating apparatus
33 upper anti-reflection film forming apparatus
40 thermal treatment apparatus
41 adhesion apparatus
42 edge exposure inspection apparatus
70 wafer transfer apparatus
110 treatment container
150 imaging unit
200 control apparatus
210 defect determination unit
211 defect information storage unit
212 defect classification unit
213 transfer way storage unit
214 defect determination table generation unit
215 defect cause identification unit
W wafer
TR transfer recipe
DT defect determination table

What is claimed is:

1. A substrate inspection method of inspecting a substrate to be repeatedly treated along a predetermined transfer way in a plurality of kinds of different treatment apparatuses, the substrate inspection method comprising:
a first imaging step of imaging a front surface of a substrate that has been treated in one treatment apparatus of the plurality of kinds of different treatment apparatuses and that is to be transferred out from the one treatment apparatus, to acquire a first substrate image;
a second imaging step of imaging a front surface of a substrate that has been an object for imaging the first substrate image, that has been treated in another treatment apparatus different from the one treatment apparatus after treated in the one treatment apparatus, and that is transferred again into the one treatment apparatus, to acquire a second substrate image;
a defect determination step of performing defect inspection, based on the first substrate image and the second substrate image, to determine presence or absence of a defect of the substrate; and
a defect cause identification step of identifying, when a defect detected from the second substrate image is not detected from the first substrate image, the defect as being caused by a treatment after the first substrate image is acquired and a treatment before the second substrate image is acquired, and identifying, when the defect detected from the second substrate image is detected also from the first substrate image, the defect as being caused by a treatment before the first substrate image is acquired, and
wherein the first imaging step and the second imaging step are performed with a substrate inspection apparatus provided in the one treatment apparatus,
wherein the one treatment apparatus provides one kind of treatment, and
wherein the one treatment apparatus includes a plurality of modules that each provide the one kind of treatment.

2. The substrate inspection method according to claim 1, further comprising:
storing a transfer way for the substrate among the plurality of kinds of treatment apparatuses when the substrate is repeatedly treated in the treatment apparatuses, into a transfer way storage;
storing information on the defect detected at the defect determination step into a defect information storage;
classifying defects stored in the defect information storage into a plurality of kinds;
generating a defect determination table in which transfer ways for the substrate stored in the transfer way storage and the kinds of the classified defects are associated; and
identifying a treatment apparatus being a cause of defect generation, based on the defect determination table, at the defect cause identification step.

3. The substrate inspection method according to claim 2,
wherein the defect determination step is performed on the same substrate for every repeated treatments, and
wherein information on the defect detected at the defect determination step repeatedly performed on the same substrate is stored in the defect information storage.

4. A non-transitory computer-readable storage medium storing a program running on a computer which controls a substrate processing system to cause the substrate processing system to perform a substrate inspection method of inspecting a substrate to be repeatedly treated along a predetermined transfer way in a plurality of kinds of different treatment apparatuses,
the substrate inspection method comprising:
a first imaging step of imaging a front surface of a substrate that has been treated in one treatment apparatus of the plurality of kinds of different treatment apparatuses and that is to be transferred out from the one treatment apparatus, to acquire a first substrate image;
a second imaging step of imaging a front surface of a substrate that has been an object for imaging the first substrate image that has been treated in another treatment apparatus different from the one treatment apparatus after treated in the one treatment apparatus, and that is transferred again into the one treatment apparatus, to acquire a second substrate image;
a defect determination step of performing defect inspection, based on the first substrate image and the second substrate image, to determine presence or absence of a defect of the substrate; and
a defect cause identification step of identifying, when a defect detected from the second substrate image is not detected from the first substrate image, the defect as being caused by a treatment after the first substrate image is acquired and a treatment before the second substrate image is acquired, and identifying, when the defect detected from the second substrate image is detected also from the first substrate image, the defect as being caused by a treatment before the first substrate image is acquired,
wherein the first imaging step and the second imaging step are performed with a substrate inspection apparatus provided in the one treatment apparatus,
wherein the one treatment apparatus provides one kind of treatment, and
wherein the one treatment apparatus includes a plurality of modules that each provide the one kind of treatment.

5. A substrate inspection apparatus of inspecting a substrate to be repeatedly treated along a predetermined transfer way in a plurality of kinds of different treatment apparatuses, the substrate inspection apparatus comprising:
a first imaging apparatus which images a front surface of a substrate that has been treated in one treatment apparatus of the plurality of kinds of different treatment apparatuses and that is to be transferred out from the one treatment apparatus, to acquire a first substrate image;

a second imaging apparatus which images a front surface of a substrate that has been an object for imaging the first substrate image, that has been treated in another treatment apparatus different from the one treatment apparatus after treated in the one treatment apparatus, and that is transferred again into the one treatment apparatus, to acquire a second substrate image; and a processor configured to perform defect inspection on the substrate, based on the first substrate image and the second substrate image, to determine presence or absence of a defect of the substrate; and identify, when a defect detected from the second substrate image is not detected from the first substrate image, the defect as being caused by a treatment after the first substrate image is acquired, and identify, when the defect detected from the second substrate image is detected from the first substrate image, the defect as being caused by a treatment before the first substrate image is acquired, and wherein the first imaging apparatus and the second imaging apparatus are provided in the one treatment apparatus, wherein the one treatment apparatus provides one kind of treatment, and wherein the one treatment apparatus includes a plurality of modules that each provide the one kind of treatment.

6. The substrate inspection apparatus according to claim 5, further comprising:

a transfer way storage which stores a transfer way for the substrate when the substrate is repeatedly treated in the treatment apparatuses;

a defect information storage which stores information on the defect detected by the processor;

wherein the processor is further configured to classify defects stored in the defect information storage into a plurality of kinds; and generate a defect determination table in which transfer ways for the substrate stored in the transfer way storage and the kinds of the classified defects are associated; and identify a treatment apparatus being a cause of defect generation, based on the defect determination table.

7. The substrate inspection apparatus according to claim 6, wherein the processor is further configured to perform the determination of the presence or absence of a defect on the same substrate for every repeated treatment, and wherein information on the defect detected by the determination of a defect by the processor repeatedly performed on the same substrate is stored in the defect information storage.

* * * * *